US005330528A

United States Patent [19]
Lazim

[11] Patent Number: 5,330,528
[45] Date of Patent: Jul. 19, 1994

[54] VASCULAR SURGICAL DEVICES

[75] Inventor: Taha R. Lazim, Glasgow, Scotland

[73] Assignee: British Technology Group Limited, London, United Kingdom

[21] Appl. No.: 859,450

[22] PCT Filed: Nov. 30, 1990

[86] PCT No.: PCT/GB90/01871
§ 371 Date: May 22, 1992
§ 102(e) Date: May 22, 1992

[87] PCT Pub. No.: WO91/07927
PCT Pub. Date: Jun. 13, 1991

[30] Foreign Application Priority Data
Dec. 1, 1989 [GB] United Kingdom ............... 8927282

[51] Int. Cl.⁵ ............................................. A61F 2/06
[52] U.S. Cl. ........................................ 623/1; 623/12; 606/194
[58] Field of Search ...................... 623/1, 11, 12; 606/191–200; 600/36; 602/13; 128/DIG. 20

[56] References Cited
U.S. PATENT DOCUMENTS

| | | | |
|---|---|---|---|
| 3,435,824 | 4/1969 | Gamponia | 623/1 |
| 4,183,102 | 1/1980 | Guiset | 623/1 |
| 4,705,517 | 11/1987 | DiPisa, Jr. | 623/1 |
| 5,156,620 | 10/1992 | Pigott | 623/1 |
| 5,171,261 | 12/1992 | Noishiki et al. | 623/1 |

Primary Examiner—David Isabella
Assistant Examiner—Debra S. Brittingham
Attorney, Agent, or Firm—Pennie & Edmonds

[57] ABSTRACT

The invention relates to a surgical device for use in operative substitution or replacement for a damaged or malformed body conduit or blood vessel, an example being an aortic aneurysm. One preferred embodiment includes a tubular body having open-end portions to provide a passageway. The wall of the body when inflated includes an annular chamber. Surrounding the body is an outer chamber of a flexible sleeve member. A probe is provided which extends forwardly of the leading end of the body, the probe providing sampling apertures to allow monitoring of body fluid flow when the device is in place. Further tubes permit inflation of the chambers. This device is suitable for insertion through the femoral artery.

12 Claims, 4 Drawing Sheets

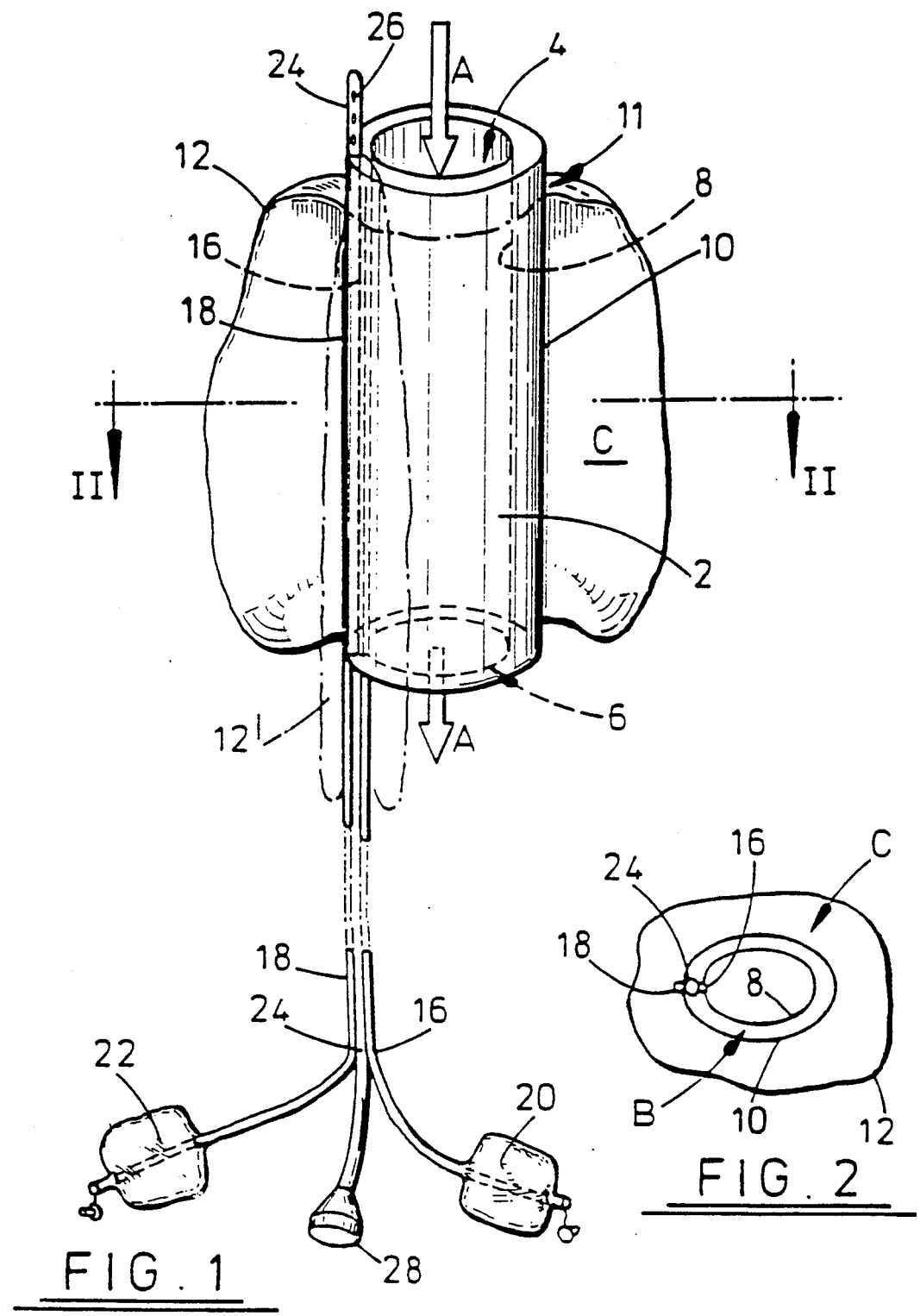

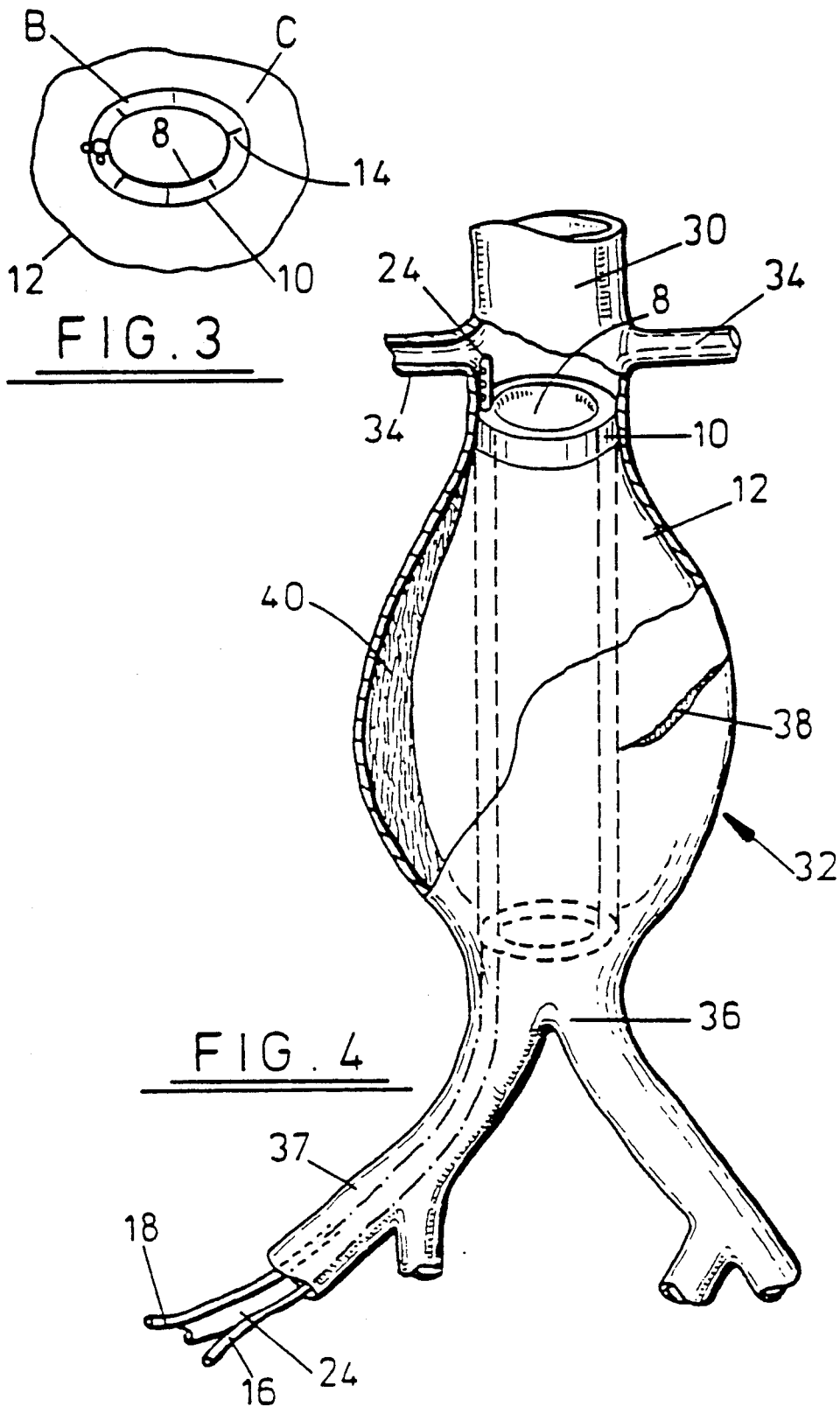

VASCULAR SURGICAL DEVICES

The invention is concerned with improvements in or relating to devices suitable for use in vascular surgery, particularly but not exclusively for use in substitution for or replacement of a damaged or malformed region of vessel or other conduit normally adapted to carry a fluid flow in mammals.

As an example of such damaged or deformed vessels, it has apparently become increasingly common over recent years for patients to suffer dilatation or sacculation of arteries, especially the aorta, to produce aneurysms which are liable to rupture. Unless suitably prompt surgery is performed, the condition is fatal. Another condition which requires surgical attention is the correction of blood flow irregularities caused by fistulae resulting from congenital deformity or from damage occurring to organs and blood vessels. In each of these two examples one of the immediate requirements is to restore a through-flow of fluid through the vessel so that fluid-pressure is not lost through leakage or other unwanted passage from the vessel.

It has generally been considered advantageous to prepare for surgery to repair or replace a region of a damaged vessel by blocking the flow of fluid to the vessel at a point slightly upstream of the region. While it is feasible in some circumstances as part of the surgical procedure to arrange an external by-pass conduit for the fluid flow during the repair procedure, in others this is virtually impossible to achieve.

While aneurysms may occur at any region of the aorta, those situated below the diaphragm, i.e. the abdominal aortic aneurysms, give the most pressing instances in which urgent surgery should be carried out if the patient is to survive. Nevertheless the general condition of the patient will probably be at a poor level due to deep shock associated with blood loss, anuria and/or low blood pressure.

It is one of the objects of the invention to provide an internal by-pass arrangement capable of maintaining, in the short, medium or long term, a fluid flow normally carried by a region of vessel or conduit rendered more or less incapable of carrying such flow.

It is another object of the invention to provide an insertion device adapted for use to connect two portions of a sound fluid flow passageway which flank a damaged or otherwise unsound region of said passageway.

The invention provides a surgical device suitable for insertion into a body fluid passageway to span a damaged or deformed portion thereof by forming communication between two relatively sound portions of said passageway spaced apart by the intervening damaged or deformed region of the passageway, said device comprising a substantially tubular body portion having open end portions, and an outer sleeve member secured at one end thereof to the body portion adjacent to one of said open end portions and secured at the other end thereof to the body portion adjacent the second of said Open end portions so as to define an annular outer chamber around said body portion, said outer sleeve member being formed from flexible material in order to allow inflation of said annular outer chamber, the body member comprising a tubular wall arrangement adapted to be in an inoperative, flaccid, condition immediately before use, means being provided for rendering the flaccid wall arrangement into a relatively rigid condition when the device is in position for use within the body fluid passageway, means also being provided for the concomitant comprising a tubular wall arrangement adapted to be in an inoperative, flaccid, condition immediately before use, means being provided for rendering the flaccid wall arrangement into a relatively rigid condition when the device is in position for use within the body fluid passageway.

The invention provides, in another of its several aspects, a surgical device suitable for insertion into a body fluid passageway to span a damaged or deformed portion thereof by forming communication between two relatively sound portions of said passageway spaced apart by the intervening damaged or deformed region of the passageway, said device comprising a substantially tubular body portion having open end portions, and an outer sleeve member secured at one end thereof to the body portion adjacent to one of said open end portions and secured at the other end thereof to the body portion adjacent the second of said open end portions so as to define an annular outer chamber around said body portion, said outer sleeve member being formed from flexible material in order to allow inflation of said annular outer chamber, the body member comprising a tubular wall arrangement adapted to be in an inoperative, flaccid, condition immediately before use, means being provided for rendering the flaccid wall arrangement into a relatively rigid condition when the device is in position for use within the body fluid passageway, means also being provided for the concomitant inflation of the annular outer chamber.

Advantageously, the tubular wall arrangement of the body member comprises an inner flexible wall portion and an outer, substantially coaxial, wall portion, said wall portions being sealed to each other at end portions thereof to form an annular wall chamber, the means to render the flaccid wall arrangement into a relatively rigid condition comprising inflation means to inflate the annular wall chamber.

Conveniently the outer wall portion of the annular wall chamber is common with and shared by the annular outer chamber, forming its inner surface.

Preferably the annular wall chamber is inflated to a pressure higher than that of the annular outer chamber, the pressure in said outer chamber being such that the sleeve member is readily conformable to the contours of the interior surface of the intervening passageway region.

Desirably, means are also provided whereby the fluid flow through the vessel and the passageway formed by the inflated tubular body portion may be monitored, together with velocity and pressure measurement and the facility of sampling the fluid for subsequent biochemical and bio-physical analyses. Conveniently, the monitoring means may include a perforated probe projecting into, for example, the blood passing through an artery or vein. Such a probe may conveniently enter the device through a sealed aperture through which also pass inflation tubes leading to the inflatable chamber(s).

In an example of a device according to the invention which is to be described below, the tubular wall arrangement comprises an inflatable annular chamber, which is to be inflated to an extent at which it becomes, reasonably rigid, may be prevented from undue distortion or "ballooning" by the provision of ties spanning the annular chamber in a radial manner to link outer and inner wall portions.

Alternatively, the annular chamber comprises a plurality of interconnected longitudinally arranged inflatable channels, conveniently having intervening plain areas.

Devices according to the invention are suitable for use in a wide range of situations. For example, a device may be used to form a conduit or a closure for a fistula which may be of a naturally occurring type such as a vascular defect affecting babies where a pre-birth pulmonary by-pass passage fails to close or, alternatively, requires to be kept open for a certain time. Other examples may be required for use as a result of injury such as a penetrative wound or pathological condition which forms a communication between the trachea and oesophagus or between an artery and a vein.

Alternatively, a device according to the invention may be used to maintain in an open condition a passageway which is at risk from closure due to a pathological condition.

While it is often convenient for a device according to the invention to be introduced through the femoral artery, it may be preferred to arrange to introduce the device through the sub-clavian artery.

Many of these examples are intended for use as short-term expedients but it is also possible to select material and situations where the device may be retained in place on a more-or-less permanent basis such as in certain forms of vascular aneurysm in the brain and inoperable vascular aneurysms.

However, the example to be described below is in the context of arterial damage, particularly in treating, often on an emergency basis, an aneurysm formed by weakness in the wall of the aorta. Aortic aneurysms may occur at any region of the aorta, those above the diaphragm being referred to as thoracic aortic aneurysms and those below being known as abdominal aortic aneurysms, (A.A.A.).

Aortic aneurysms are frequently the result of the effects of arterio-sclerosis and expanded to the point of rupturing by high blood pressure levels. Thus the condition of the arteries in patients is frequently poor and many patients who receive successful operative treatment for the ruptured aneurysm nevertheless die from myocardial infarction, renal or multiple organ failure especially as emergency surgery is usually carried out on a patient who is in a state of deep shock.

Correcting the effect of shock due to rupture of the aneurysm is difficult in emergency operations when there is a continuous leakage of blood from the tear in the artery wall at the site of the aneurysm. Many attempts have been made to stem the flow through the aorta long enough to permit the tear to be closed. Devices such as inflatable plugs or catheters inserted into the upstream neck of the aneurysm may be more effective than simply clamping and closing the aorta, but either of these techniques stops the supply of blood to the pelvis and lower limbs. In some cases it is possible during surgery to provide an external by-pass conduit but such procedures do not allow stabilisation of the patient's condition prior to surgery. Serious risks still remain in that shock, metabolic abnormalities or deficiencies in heart, lung and kidney functions are not ameliorated prior to surgery. Similarly, the presently available range of devices does not allow immediate restoration of blood flow to the lower limbs and therefore damage may be still present there after successful surgery.

It would therefore be advantageous for the surgery necessary for repair of the ruptured aneurysm to be delayed until the patient's condition has stabilised and he/she has come out of shock. A device according to the invention may be used to achieve this aim.

There will now be described in detail two examples of a device according to the invention. It will be understood that the description, which is intended to be read with reference to the drawings, is given by way of example only and not by way of limitation.

In the drawings:

FIG. 1 shows a perspective view partly in section, of the first device in a inflated condition, FIG. 2 is a cross-sectional view on line II—II of FIG. 1, to a slightly smaller scale;

FIG. 3 is a view similar to that of FIG. 2 of a modification of the device;

FIG. 4 is a perspective view, partially in section of the device in position in an association with an aortic aneurysm;

Figure 5:
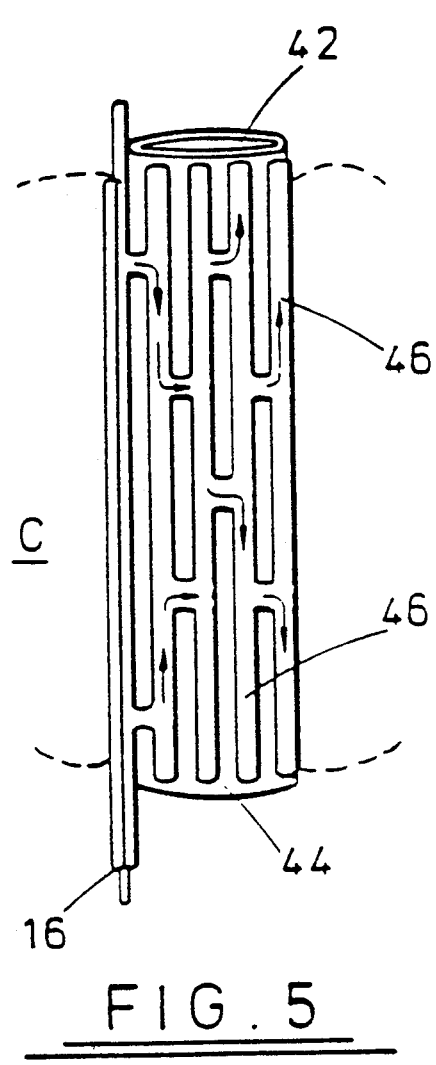
FIG. 5 shows an alternative constriction of an inner wall portion of the first device.

The first device comprises an inflatable tubular body 2 having open end portions 4, 6 to provide a passageway therethrough in the direction shown by arrows A. The tubular body 2 comprises an inner wall portion 8 and an outer wall portion 10 which in the present example are of reinforced polyvinylchloride sheet material, each portion being sealed at said end portions to the other portion to form an annular wall chamber B. It will be understood that other bio-compatible materials may also be utilised.

Attached to the outer wall portion 10 at two circumferential regions thereof, each spaced inwardly of the end portions 4, 6 respectively to form a shoulder at 11, is a sleeve member 12 which in the present example is of polyurethane sheet material, and which together with an outer surface wall portion 10 defines an annular outer chamber, C, as shown in FIGS. 2 and 3.

The chambers are adapted to be inflated as will be explained below, the modification shown in FIG. 3 including wall tie members 14 adapted to reduce any tendency for distortion of the chamber B by undue ballooning of the wall portions 8 and 10.

The device described in the present example is provided with two independent inflation means comprising a supply pipe 16 adapted for use in the controlled inflation of chamber B and a supply pipe 18 for the controlled inflation of chamber C. Monitoring sacs 20, 22 allow the user to check the state of inflation from the pipes 16, 18, respectively, although the pipes may be connected to other equipment for accurate measurements of inflation pressures.

The two pipes are formed into an assembly with a hollow flexible probe 24 comprising a tube having a plurality of sampling apertures 26 at a leading end thereof which conveniently projects beyond the end portion 4 of the wall portions 8, 10 of chamber B so as to have access to the fluid flowing in the direction of arrow A, upstream of the device. Sampling apparatus may be attached to the probe 24 at an outer end 28 thereof. Conveniently the probe arrangement may be used for monitoring blood pressure, taking samples, in angiography, or in association with other sensors.

FIG. 4 shows the device in use in a situation involving an abdominal aortic aneurysm. The aorta 30 has formed an aneurysm 32 at a region below the renal arteries 34 and above the bifurcation of the aorta at 36. The aneurysm has a tear 38 in the wall thereof and a quantity of thrombus 40 is present within the aneurysm.

The device is in a completely deflated condition in which both chambers B and C are flaccid, taking up the general outline 12 shown in chain dotted lines in FIG. 1. An incision is made in one of the femoral arteries 37 and the device introduced so as to enter the aneurysm. The probe 24 acts to support the flaccid chambers during this procedure, the leading end of the probe acting as a pilot portion. It is convenient if the leading end of the probe is equipped with sensor means to detect the change in blood pressure velocity or pattern of flow at the region of the entrances to the renal arteries to confirm that the device has been inserted into the required position. However, this is not an essential requirement.

As soon as the surgeon is satisfied that the device is correctly positioned, the chambers B and C may then be inflated. Chamber B is inflated and takes up the desired tubular shape as shown in FIG. 4, in which its upper end portion 6 is arranged so that the aorta 30 is substantially or completely blocked by its presence, forcing the blood to flow through the passageway bounded by a tubular wall arrangement which is by now firm and effectively rigid. It will be appreciated that this positioning and blocking is aided by the provision of the shoulder 11 formed at the seam between wall portions 10 and 12.

Inflation of chamber C through the line 18 meanwhile causes the sleeve member 12 to conform to the shape of the aneurysm allowing for the presence of thrombus. Thus the tear 38 is sealed by the wall portion 12 and the aneurysm generally supported by the inflated chamber C. However, chamber C is inflated to a pressure level, say, 20–50 mm Hg, less than that required for the chamber B which may be 100–150 mm Hg.

Figure 6:
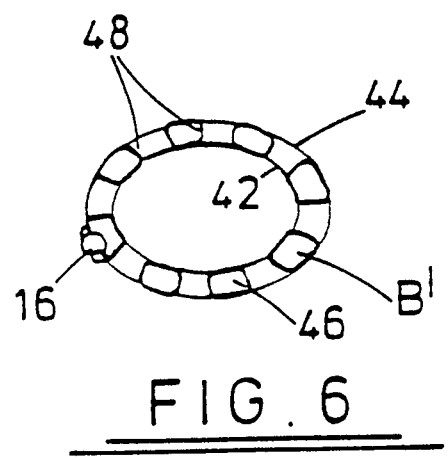
FIGS. 6 and 7 are cross-sectional views of the wall potion as shown in FIG. 5 and in an alternative construction, respectively.
Figure 7:
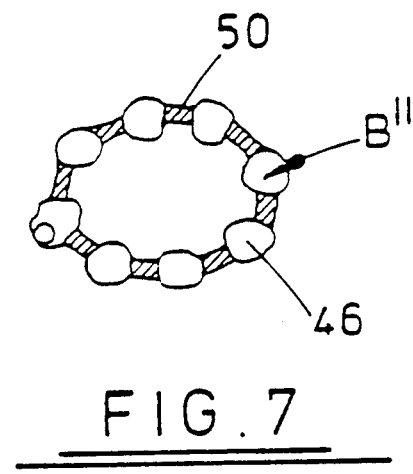

FIGS. 5 to 7 show two alternative forms of construction of chamber B to that illustrated in FIGS. 1 to 4. Chamber B' comprises an inner wall 42, and an outer wall 44 that is common to the outer chamber C. However, a series of longitudinally disposed, interconnected passages 46 are formed by webs 48 spanning the annular chamber, the passages alone being inflated. It will be observed that the passages 46 are no wider than the intervening areas of wall 42,44. In FIG. 7, the passages 46 are defined by intervening solid wall portions 50, the passages 46 comprising the chamber B''.

Figures 8, 9:
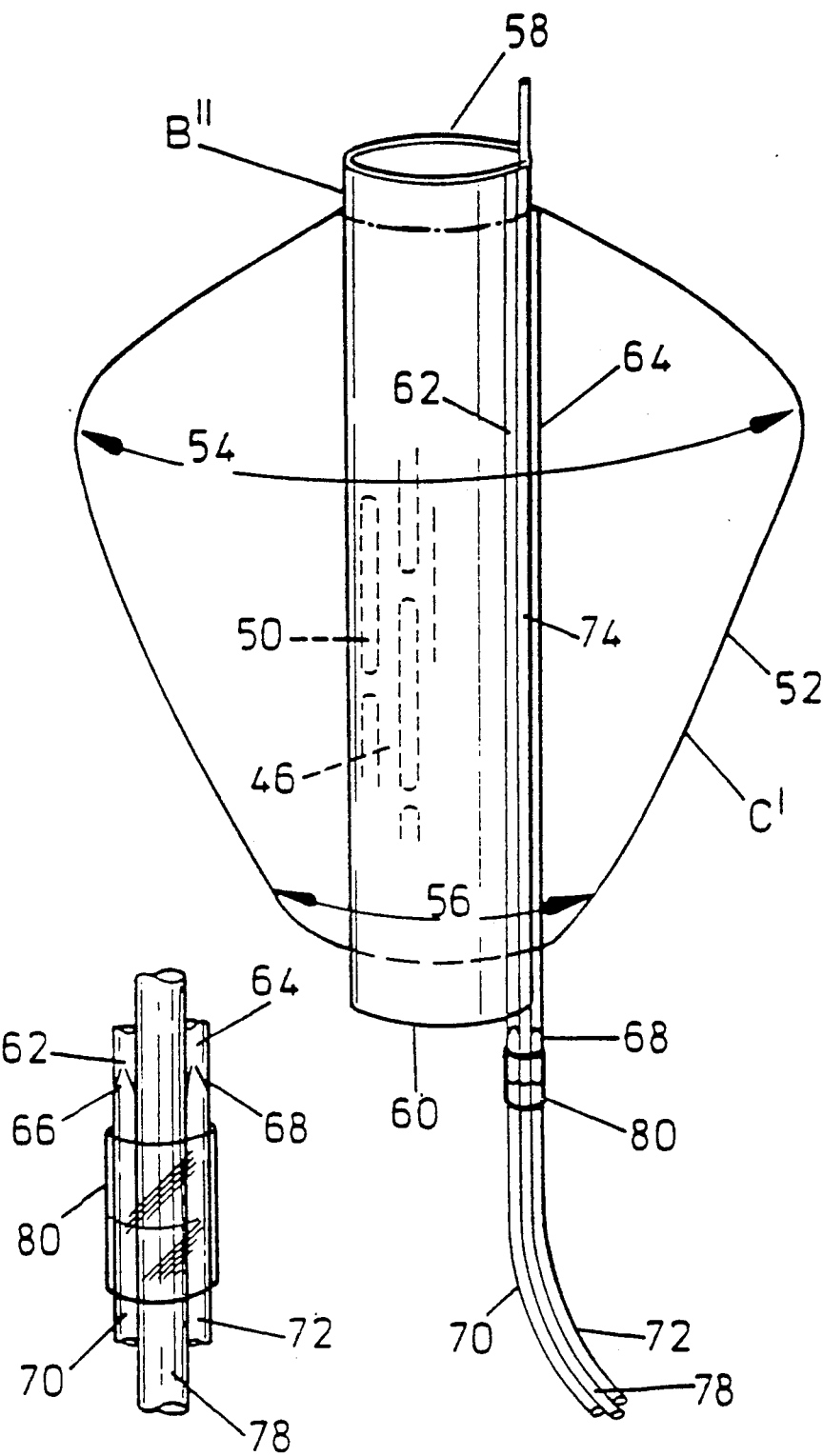
FIG. 8 shows a second example of a device according to the invention.
FIG. 9 is a fragmentary portion of the device of FIG. 8 to an enlarged scale.

FIG. 8 shows an alternative arrangement which is suitable for use in many circumstances and is particularly suitable where the device is introduced through the sub-clavian artery. It appears that the device illustrated has the advantage of minimising the further quantity of blood entering the aneurysm. The device shown in FIG. 8 comprises a chamber B'' of the construction shown in FIGS. 5 and 7 comprising passages 46 and having intervening solid wall portions 50. Chamber C' is defined by the outer surface of chamber B'' and an outer wall 52 which is flexible but substantially inelastic. It is arranged that chamber B'' projects at each end, beyond the chamber C. The shape of the wall 52, when inflated gives an area of widest diameter at 54 (approximately 55 mm in one example) tapering downwardly to about 30 mm at the area 56. It will be observed that the widest diameter at 54 is approximately at a level one third of the distance (60 mm) from the leading end 58 of the device to the trailing end 60. It has been found that the formation of the chamber at 54 tends to prevent displacement of the device in use, by normal blood flow.

The inflation and sampling means of FIGS. 8 and 9 will now be described. This comprises a supply pipe 62 for inflating the passages 46 of chamber B'' and a supply pipe 64 for inflating the chamber C. Each pipe 62, 64 is provided with a one-way valve 66,68, at a region adjacent a joining zone between the pipes 62 and 64 and extensions 70 and 72 which are connected at their remote ends to a source of $CO_2$ gas. A sampling probe 74, the leading end 76 of which projects beyond the leading edge 58 of the device, is also provided with an extension 78, the three extensions being joined by suitable means at 80. It will be understood that the extension 78 is provided at its remote end with a sampling connector to attach to a clinical syringe.

It is important to note the possible advantages which may accrue from the use of flexible but relatively inelastic material for the chamber walls. Thus the shape of the chamber C' when inflated may be carefully controlled as to contour and size by its actual manufacture rather than by the degree of inflation to which it is subjected.

The device thus forms an internal by-pass for the aortic blood flow and may remain in place temporarily at least until the condition of the patient has stabilised so that conventional surgical techniques may be applied, for example the replacement of the damaged region of the vascular wall by a graft of suitable plastics material. If, however, the patient's condition is such that further surgery is inadvisable, then the device according to the invention may remain in place for a much longer period. Suitable materials will be chosen to permit such an option to be available, that is, materials which do not cause adverse reaction when in situ. Where the device is intended to be effectively permanent, the conduit holding the lines 16 and 18, together with the monitoring probe, may be disconnected at a suitable location.

In the above example a device has been described which includes two inflatable chambers, one inflated to a pressure level such that a reasonably rigid tubular passageway is achieved and the other, surrounding the first, to assist in sealing and supporting damaged areas. It will be understood that in situations in which it is necessary simply to provide a passageway to replace a section of body conduit, only one tubular chamber need be provided.

Various modifications may be made within the scope of the invention as defined by the following claims.

I claim:

1. A surgical device suitable for insertion into a body fluid passageway to span a damaged or deformed region thereof by forming communication between two relatively sound portions of said passageway spaced apart by the intervening damaged or deformed region of the passageway, said device comprising a substantially tubular body member having open end portions, and an outer sleeve member secured at one end thereof to the body member adjacent to one of said open end portions and secured at the other end thereof to the body member adjacent the second of said open end portions so as to define an annular outer chamber around said body member, said outer sleeve member being formed from flexible material in order to allow inflation of said annular outer chamber, the body member comprising a tubular wall means defining annular inner chamber means and adapted to be in an inoperative, flaccid, condition immediately before use, means being provided for rendering the flaccid wall means into a relatively rigid condition when the device is in position for use within the body fluid passageway, means also being provided for the concomitant inflation of the annular outer chamber.

2. A surgical device suitable for insertion into a body fluid passageway to span a damaged or deformed region thereof by forming communication between two relatively sound portions of said passageway spaced apart by the intervening damaged or deformed region of the passageway, said device comprising a substantially tubular body member having open end portions, and an outer sleeve member secured at one end thereof to the body member adjacent to one of said open end portions and secured at the other end thereof to the body member adjacent the second of said open end portions so as to define an annular outer chamber around said body member, said outer sleeve member being formed from flexible material in order to allow inflation of said annular outer chamber, the body member comprising a tubular wall means adapted to be in an inoperative, flaccid, condition immediately before use, means being provided for rendering the flaccid wall means into a relatively rigid condition when the device is in position for use within the body fluid passageway, means also being provided for the concomitant inflation of the annular outer chamber; and wherein the tubular wall means of said body member comprises an inner flexible wall portion and an outer, substantially coaxial wall portion, said wall portions being sealed to each other at end portions thereof to form an annular wall chamber, the means to render the flaccid wall means into a relatively rigid condition comprising inflation means to inflate the annular wall chamber.

3. A device as claimed in claim 2, wherein the inner wall portion and the outer wall portion are connected together at intervals by web portions spanning the wall portions.

4. A device as claimed in claim 3, wherein the web portions are arranged to provide a series of longitudinally disposed, interconnected passages.

5. A device as claimed in claim 1, wherein the tubular wall means of the body portion comprises a flexible wall portion having passages formed therein with intervening solid wall portions, the means to render the body portion into a relatively rigid condition comprising inflation means to inflate the passages in the flexible wall portion.

6. A device as claimed in claim 2, wherein the outer wall portion of the annular walled chamber is common with and shared by the annular outer chamber, forming its inner surface.

7. A device as claimed in claim 6, wherein the material from which the outer chamber is formed is readily conformable in use to the contours of the interior surface of said intervening body fluid passageway region.

8. A device as claimed in claim 6, wherein the material from which the outer chamber is formed is inelastic.

9. A device as claimed in claim 8, wherein the outer chamber in its inflated condition adopts a double-cone configuration in which each cone has a base merging with the base of the other cone in an annular region.

10. A device as claimed in any one of the preceding claims, in which there are provided monitoring means including a perforated probe projecting beyond a leading end portion of the device and including a tubular conduit to a sampling apparatus.

11. A device as claimed in claim 10, wherein the probe provides support for the inflation means.

12. A surgical device suitable for insertion into a body fluid passageway to span a damaged or deformed region thereof by forming communication between two relatively sound portions of said passageway spaced apart by the intervening damaged or deformed region of the passageway, said device comprising:
(a) a substantially tubular body member having a longitudinal axis and comprising a tubular wall means defining a first inner chamber means arranged in an annular configuration along said longitudinal axis and adapted to be in an inoperative, flaccid, condition immediately before use and having first and second open end portions along said longitudinal axis;
(b) an outer sleeve member secured at one end thereof to the body member adjacent to said first open end portion and secured at the other end thereof to the body member adjacent the second open end portion so as to define a second annular outer chamber surrounding said body member with said second chamber being isolated from said first chamber;
(c) said outer sleeve member being formed from flexible material in order to allow inflation of said annular outer chamber;
(d) means for rendering said flaccid tubular wall means into a relatively rigid condition when the device is in position for use within the body fluid passageway; and
(e) means for the concomitant inflation of the annular outer chamber.

* * * * *